United States Patent [19]

Klug

[11] Patent Number: 5,263,946

[45] Date of Patent: Nov. 23, 1993

[54] LATEX URINE CONTAINER HAVING ODOR IMPERMEABLE TREATMENT AND PROVIDED WITH INTEGRAL STRAP HOLDERS

[75] Inventor: K. Robert P. Klug, Tucson, Ariz.

[73] Assignee: Sierra Laboratories, Inc., Tucson, Ariz.

[21] Appl. No.: 834,859

[22] Filed: Feb. 13, 1992

Related U.S. Application Data

[63] Continuation-in-part of Ser. No. 695,903, May 6, 1991, abandoned.

[51] Int. Cl.$^5$ .......................... A61M 1/00; A61F 5/44; A61B 5/00; B65D 33/00
[52] U.S. Cl. ........................ 604/327; 128/760; 128/767; 604/329; 604/349
[58] Field of Search ............... 604/327, 328, 329, 317, 604/330, 331, 346–347, 349–353; 128/760, 842, 761, 844, 767, 918; 4/144.1, 144.2; 224/222, 267; 428/35.7, 36.6, 36.7, 36.8

[56] References Cited

U.S. PATENT DOCUMENTS

| | | | |
|---|---|---|---|
| 4,846,816 | 7/1989 | Manfredi | 604/349 |
| 4,976,816 | 12/1990 | Coye | 269/37 |
| 5,153,039 | 10/1992 | Porter et al. | 428/36.8 |

Primary Examiner—Randall L. Green
Assistant Examiner—A. Zuttarelli
Attorney, Agent, or Firm—Victor Flores

[57] ABSTRACT

A latex container for use as a leg bag by urinary incontinent persons. The latex leg bag is provided with strap holders that are formed simultaneously with the leg bag structure to provide a more structurally reliable strap holder. The strap holder includes a nodal growth of latex, simultaneously grown during the latex coagulation process. The nodal growth bridges an interstice on the former to close the strap holder loop. The leg bag container is provided with a skewed entry neck for facilitating better dressing of the delivery tube during use, and may be formed in a concave shape to better conform to the user's leg. The former is machined with corresponding structure to form the leg bag in a latex coagulation process. After the latex bag is formed and cured for a predetermined period, the latex bag structure is treated with a rubber polymer/solvent (KRATON G/toluene) chemical compound for managing the permeation of urine odors.

15 Claims, 3 Drawing Sheets

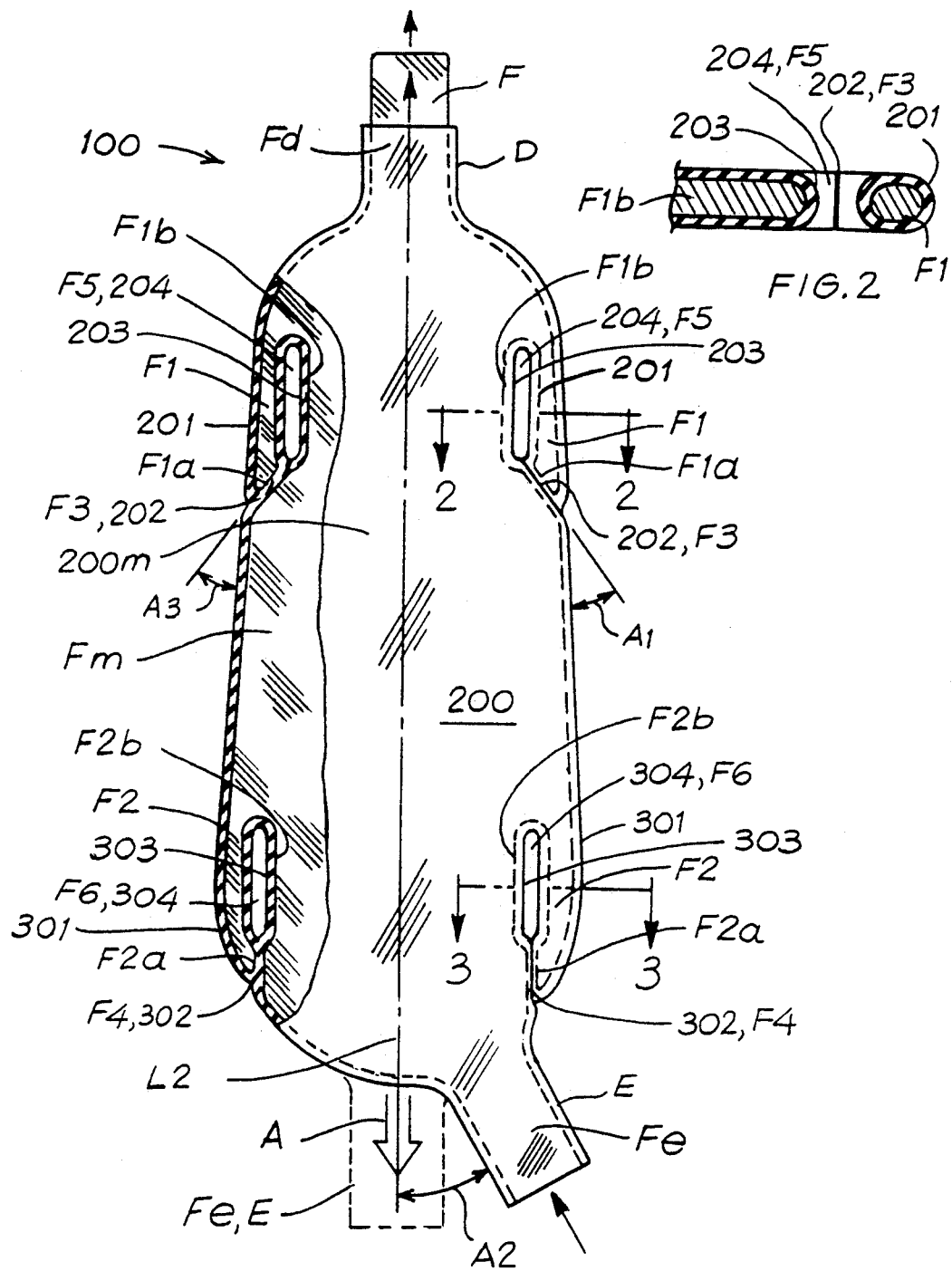
FIG. 1
FIG. 2
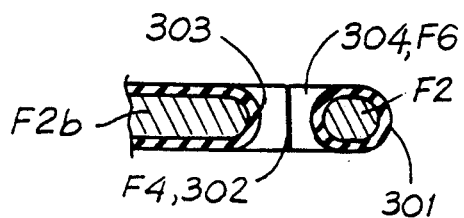
FIG. 3

LATEX URINE CONTAINER HAVING ODOR IMPERMEABLE TREATMENT AND PROVIDED WITH INTEGRAL STRAP HOLDERS

RELATED APPLICATIONS

This application is a continuation-in-part of U.S. patent application Ser. No. 07/695,903, now abandoned as of Feb. 15, 1992, filed on May 06, 1991.

FIELD OF THE INVENTION

The present invention relates to latex container apparatus and associated strap holders, methods of forming the strap holders, and container structures treated with polymers for managing permeation of odors from within. More particularly, the present invention relates to latex urinary bags of the type having strap holders formed concurrently with the container body, and that have structure treated with a rubber polymer coating for managing permeation of urine odors from within.

DESCRIPTION OF THE PRIOR ART

Latex leg bags are used by incontinent persons to control urinary discharge. The nonporous characteristic of latex results in its wide use for producing leg bags for the incontinent person. The elongated portion of the bag is generally attached to the leg of the individual at the thigh or calf areas using the bag's strap holders and attachment strapping.

The latex leg bags are typically formed using aluminum formers having a flat oval shape that produce similarly shaped bags. Although concave shapes are desirable for better conformity to a user's leg, the flat shapes have been accepted for use in that the pliable nature of the latex material can generally be relied upon for conforming the flat pliable bag structure to the person's leg area. In attaching the bag, a user also relies upon the straps holders provided on the bag, in combination with auxilliary straps that encircle the leg, for supporting the bag while being used.

Presently known, and commercially available leg bags provide entry and drain necks that are straight and oppose each other and are in substantial alignment with the central axis of the elongated bag portion. The entry neck port houses associated check valve and tubing that is detachably connected, by example, to the male user's penis. Although the straight orientation of the entry neck with respect to the drain neck port has been accepted by the user, a skewed orientation with respect to the central axis of the elongated bag is preferred because such orientation results in facilitating a more natural placement of the interconnecting tubing and also avoids tube kinking.

The strap holders provided on leg bags have been traditionally provided on the bag by bonding latex strips to the bag using adhesives. The adhesive bond has not provedn reliable during the life of the latex bag, notwithstanding the special manufacturing effort involved in effecting the bonding of the latex strips. Improvements in providing the strap holders as integral holding straps are taught in U.S. Pat. No. 4,976,816 wherein two semi-cured latex components, namely a preformed strap holder strip and the latex bag, are affixed together. The two surfaces are wetted with uncured latex prior to mating the surfaces and held together using mechanical jigs during the curing process. Although referred to as integral holding straps, the body structures of the holding strap, the corresponding portion of the bag and the connecting joint are formed at separate times and are not believed to be an integral holding strap. The manufacturing steps in producing two separate latex components and the manipulation procedures to effect the latex joint between the holding straps and the bag are viewed as a cost disadvantages. The integral holding strap as taught by U.S. Pat. No. 4,976,816 lacks the simultaneity in formation to effect a more structurally reliable strap holder.

Although the latex bag is recognized for its rugged, secure construction and economical reuse characteristics, one drawback seen by latex urine bag users is the undesirable high rate of urine odor permeation associated with the latex rubber. The high rate of urine odor permeation requires great care from the user to control the odor. Typically, the latex bag must be cleaned with bleach or commercial disinfectants on a regular basis and then dried, thus multiple bags are required to accommodate the user's needs. Some users have been known to wrap the bag with duct taping as a way of managing the permeation of the urine odor. Alternatively, urine bag users use polyvinyl chloride (pvc) bags because of the impermeability of pvc to urine odors. The pvc urine bag user has to contend with the frequent disposal costs and the less reliable construction of the pvc bags when compared with the latex urine bag. Another alternative to latex urine bags is butyl rubber bags which are costly, due to the die-cut/bonded/cured construction, but are however, highly impermeable to the urine odor. To applicant's knowledge butyl rubber urine bags are rarely used. Also to applicant's knowledge, there is no prior art relating to latex urine bags which are treated to manage the urine odor permeation.

Therefore, a need is seen to exist for an improved container for use as a leg bag by urinary incontinent persons.

More particularly, a need is seen to exist for an improved latex container for use as a leg bag by urinary incontinent persons, that is provided with strap holders that are formed simultaneously with the leg bag structure to provide a more structurally reliable strap holder and which bag structure is treated with a chemical compound for managing the permeation of urine odors.

Even more particularly, a need is seen to exist for an improved latex container for use as a leg bag by urinary incontinent persons, that is provided with strap holders that are formed simultaneously with the leg bag structure and that is also provided having a skewed entry neck for providing better delivery tube dressing and a concave shape to better conform to the user's leg and which has been treated with a chemical compound for managing the permeation of urine odors.

A related need is seen to exist for a mold/former and method for producing the above needed latex container.

SUMMARY OF THE INVENTION

Accordingly, the primary object of the present invention is to provide a latex container having strap holder means that are formed simultaneously with the leg bag structure and which has been treated with a chemical compound for managing the permeation of urine odors.

A closely related object of the present invention is to provide a mold, referred to hereinafter as a former, having structure for producing the latex container.

Another related object of the present invention is to provide a method for using the former in a latex coagulation process for producing the latex container.

Another object of the present invention is to provide a latex bag container having a skewed entry neck for facilitating better dressing of the delivery tube and also having a concave shape to better conform to the user's leg.

The foregoing objects are accomplished by providing an aluminum former for being dipped into a latex emulsion for forming the latex container. The aluminum former includes a body portion, for forming an elongated bag portion, at least one protruding machined portion, for forming at least one strap holder, and an interstice portion provided at a distal end of the at least one protruding machined portion that facilitates formation of a latex nodal growth during the latex coagulation process. The elongated bag body portion and the at least one strap holder, including the nodal growth, being a uniform simultaneously formed bag structure. The machined interstice portion provided at the distal end the protruding machined portion facilitates the formation of a latex nodal growth during the latex coagulation process that bridges the end of the strap holder, back to the body of the elongated bag portion. The strap holder, including the nodal growth, and an opposing portion of the body of the elongated bag delineate a slot for receiving a support strap used to attach to a user's leg. The former may include several of the protruding portions to produce as many of the strap holders as are deemed necessary It has been determined that an upper and lower set of two laterally opposed strap holders are adequate to support the bag. Further, the end of the former that defines the entry neck of the bag apparatus may be machined to provide a skewed potion that will form a similarly skewed entry neck on the latex bag for facilitating better dressing of the delivery tube. Also, the former may be provided having a concave shape for producing the leg bag having a concave shape to better conform to the user's leg.

After formation of the latex bag and removal from the former, the formed latex bag is oven dried in preparation for treatment with a suitable concentration of a highly impermeable chemical compound to counter the problem of high rate of urine odor permeation, normally associated with untreated latex bags. The impermeable chemical compound treatment is preferably in the form of a coating deposited on the latex bag, which coating is optionally formed on the bag's exterior or interior surface, or both.

Therefore, to the accomplishments of the foregoing objects, the invention consists of the foregoing features hereinafter fully described and particularly pointed out in the claims, the accompanying drawings and the following disclosure describing in detail the invention, such drawings and disclosure illustrating but one of the various ways in which the invention may be practiced.

BRIEF DESCRIPTION OF THE DRAWINGS

FIG. 1 is a partially cutaway plan view of a flat structured leg bag (container) according to the present invention shown in a formed state with the former (mold) used to produce it in a latex coagulation process.

FIG. 2 is cross-sectional view of the former and corresponding strap holder portion at the leg bag's drain-end taken along line 2—2 in FIG. 1.

FIG. 3 is cross-sectional view of the former and corresponding entry-neck-end, strap holder portion taken along line 3—3 in FIG. 1.

DESCRIPTION OF THE PREFERRED EMBODIMENT

Figure 4:
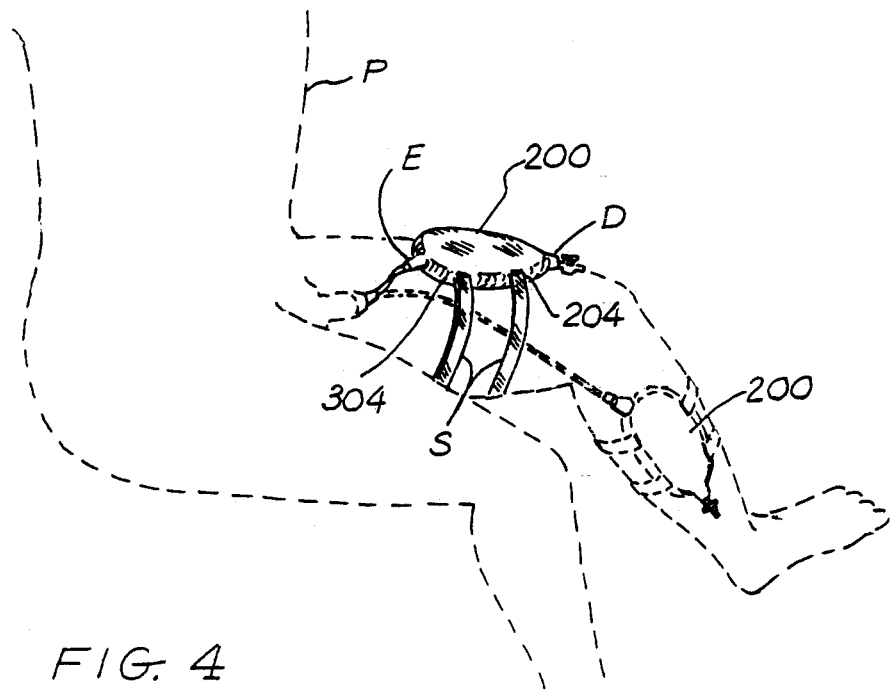
FIG. 4 is an application view of the present invention showing the latex container (leg bag) and strap holders attached to a male user at two possible leg locations.

In accordance with the objects of the present invention, FIG. 1 depicts a combined apparatus 100 showing the former (mold) F and the leg bag 200 formed thereon. The former F comprises a main body portion Fm for forming the main elongated bag portion 200m. The former also comprises laterally opposed and longitudinally spaced protruding machined portion F1, F2 for forming, similarly located, strap holder formations 201, 301. Former F is machined having interstice portion F3, F4 at a distal ends F1a, F2a of protruding portions F1, F2 that facilitate formation of latex nodal growths 202, 302 during a latex coagulation process that forms bag 200. Protruding portions F1, F2, in combination with opposing former portions F1b, F2b and interstice portions F3, F4, delineate openings F5, F6. Similarly, strap holder formations 201, 301, in combination with corresponding opposing portions 203, 303, of said main elongated bag portion 200m, and nodal growths 202, 302, delineate openings 204, 304 for receiving attachment straps S (see FIG. 4). Former F includes an entry neck portion Fe machined skewed at an angle A2 with respect to central longitudinal axis line L2 to form a similarly skewed bag entry neck E. The orientation of former entry neck portion Fe and bag entry neck E may also be provided as shown in alignment with line L2 and directly opposite the former drain neck portion Fd and the bag's drain neck D. The bag 200 is removable from former F in the direction as shown by arrow A. To facilitate this removal, the entry neck-end set of laterally spaced and opposing interstices F4 and nodal growths 302 are oriented substantially parallel with longitudinal axis line L2 while the drain-end set of laterally spaced and opposing interstices F3 and nodal growths 202 are skewed at angles A1 and A3 from longitudinal axis line L2.

As illustrated in cross section in FIGS. 2 and 3, the formation of leg bag 200 onto former F that occurs during the latex coagulation process results in simultaneous formation of opposing portions 203, 303 onto former portion F1b, F2b, strap holders 201, 301 onto protruding machined portion F1, F2 and formation of nodal growths 202, 302 in interstices F3, F4. The formation results formation of loop opening 204, 304 congruent with former openings F5, F6.

FIG. 4 show a person P in a sitting position with the leg bag 200 according to the present invention attached to the left thigh using a pair of straps S looped through openings 204, 304. FIG. 4 also shows leg bag 200 apparatus worn in an alternative position about the left calf of person P.

Figure 5:
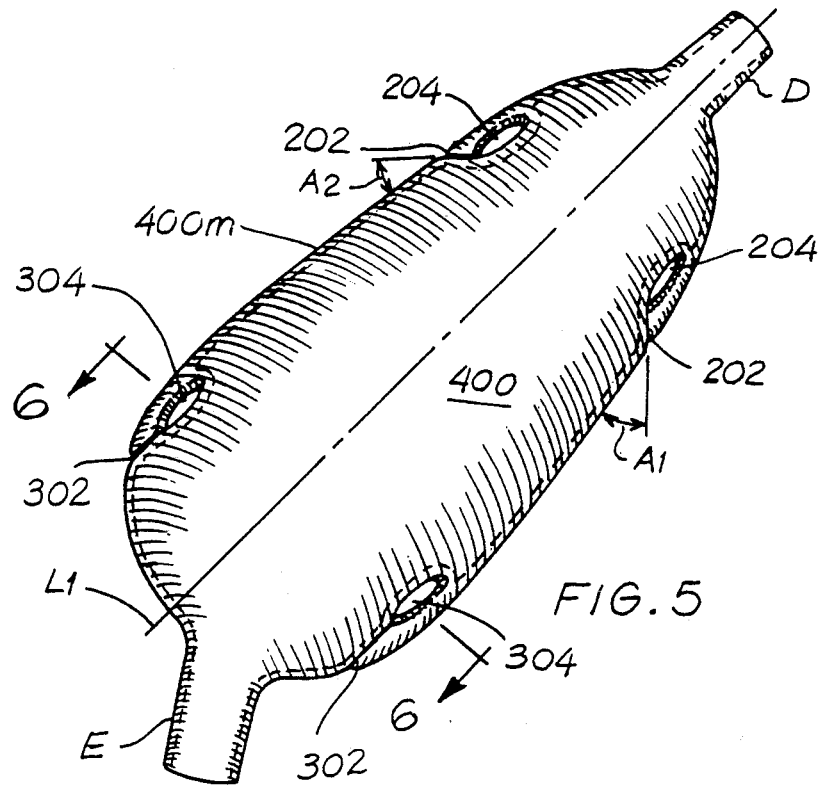
FIG. 5 is a plan view of a concave latex container according to the present invention illustrating the skewed entry neck and opposing sets of laterally spaced strap holders that were simultaneously formed with the illustrated leg bag.

FIG. 5 shows a curved leg bag 400 formed using a similarly shaped former F. Leg bag 400 is provided such that its concave portion will conform to the shape of a leg of the wearer. Aside from the concave structure, leg bag 400 comprises all of the features of leg bag 200 illustrated in FIG. 1., namely skewed entry neck E, nodal growths 302 in substantial parallel relationship with longitudinal axis line L1, strap holder openings 304, skewed nodal growths 202 and strap holder openings 204, all aspects being uniformly formed, including drain neck D.

Figure 6:
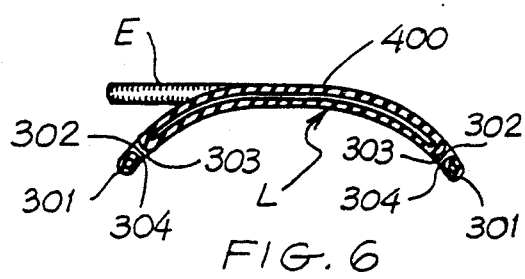
FIG. 6 is a cross-sectional view of the leg bag taken along line 6—6 in FIG. 5 illustrating the concave leg bag structure, the skewed entry neck port and the laterally opposed strap holders, including the nodal growth and slot portions.

FIG. 6 shows a cross-sectional view taken along line 6—6 in FIG. 5 and illustrates the uniformity of the simultaneous formation of the leg bag 400, preferably from latex material L, and further illustrates the elements of the invention, including the laterally opposing strap holders 301, openings 304, nodal growths 302, and opposing elongated body portions 303.

While, the art of forming leg bags is well known, the formation of leg bags according to the present eliminates the need for ancillary jigs, and associated costs, in that only one former F is required to produce a leg bag the accomplishes the total need of urinary incontinent male, preferably a former F that produces bag 400, although a flat shaped former F is not objectionable. Accordingly, the steps required to produce a leg bag 200, 400 according to the present invention include: (a) providing an aluminum dipping former F (mold), former F having at least one protruding machined portion F1, F2 for forming at least one strap holder 201, 301 and also having a corresponding machined interstice portion F3, F4 provided at a distal end F1a, F2a of said at least one protruding machined portion F1, F2 for facilitating formation of nodal growths 202, 302 during a coagulation process of latex that forms the latex leg bag; (b) providing an alcohol coagulant solution for dipping said former F in preparation for dipping into a latex emulsion; (c) providing a latex emulsion; (d) dipping said prepared former F into the latex emulsion to begin the coagulation process; (e) forming the latex leg bag, including simultaneously forming an elongated bag portion 200m, 400m, at least one strap holder 201, 301 on said at least one protruding machined portion F1, F2 and said nodal growth 202, 302 by coagulation buildup during said coagulation process until interstice F3, F4 is bridged, such that the nodal growths 202, 302 extend outwardly from the slot periphery towards the outer periphery of the container; and (f) curing and removing said formed latex leg bag 200, 400 from said former F.

After the latex bag has been dried, typically for a twelve (12) hour period at 140 degrees F., the latex bag is further manipulated in preparation for treatment in a chemical compound for managing the permeation of urine odors, i.e. properly placed on solution dip pegs with its normally used exterior surface exposed, or in an alternative manner, the bag is manipulated inside-out with its interior surface exposed. The chemical compound may be a rubber polymer, such as butyl rubber, solvated in a hydrocarbon solvent, such as toluene, to form a cement for dipping the latex bag. While butyl rubber has superior impermeability properties, there are process problems which detract from its use, namely that blisters are formed on the latex surface, trapping the vaporized solvent, due to the high curing temperature required for butyl, on the order of 400 degrees F., and which high temperature scorch the latex rubber.

Thus, the preferred embodiment utilizes a rubber polymer known commercially as KRATON G, (a registered trademark of Shell Chemical Co.), solvated in a concentration consisting of 8% (eight percent), by weight, of the KRATON G rubber polymer, in toluene solvent. The 8% KRATON G/toluene cement solution has been found to yield a viscosity that suitably reduces the entrapment of air during emersion and that also minimizes dripping during extraction, and which can be cured at lower temperatures than butyl, typically 140 degrees F., or in an air stream at room temperature. Other solvents, such as xylene may produce the desired viscosity, but is characterized in that the evaporation rate is too slow for industrial applications. Mixtures of different solvents is also possible but tend to produce blistering due to the solubility parameters, vapor pressures and different flashing-off rates from the KRATON G rubber polymer. The toluene solvent does not impact the molecular structure of the KRATON G rubber polymer, i.e. the styrene-ethylene/butylene-styrene molecular block structure is reorganized after the dipping process. The impermeability to gases and liquids of the KRATON G compares better than the vinyl chloride polymers and is less than that of butyl rubber. Other notable features found when dipping the latex bags with the KRATON G rubber polymer, aside from the excellent impermeability properties associated with gases and liquids, such as urine, include: (1) an elasticity that is comparable to the latex (approximately 700% elongation), and thus delamination is not a concern, (2) adherence to the latex substrate is very good due to a mechanical bond formed after a swelling of the latex during the dwell period of the bag in the solvent, (3) repair is made easy due to being easily applied using a brush and cured at room temperature, (4) toxicity is not a concern (KRATON G-1657 the particular KRATON G series preferred by applicant, is used in medical and food contact applications), and (5) a higher yield is possible in that rejects can be treated with the solvent and redipped.

Because of the solvent required in the process, suitable safety precautions must be strictly followed to assure the health and welfare of all persons in the process, as well as protecting the environment.

As noted above, the bag is manipulated with the desired interior/exterior surface exposed, and readied for the dipping process in accordance with the foregoing describe rubber polymer/solvent cement. Typically, the latex bag is dipped in the cement for 4 minutes and then withdrawn to allow the solvent to flash off leaving a thermoplastic film. In the preferred embodiment, the toluene will flash off in about 5 minutes when the dipped bag is placed in an air stream at room temperature or in an oven at 140 degrees F. The bag is then immersed again and extracted very quickly without allowing any dwell in the cement. The toluene is flashed off, typically requiring five minutes as noted above. The dipping is repeated until a desired thickness of the thermoplastic film is produced, a 5 millimeter thickness of the KRATON G thermoplastic requires 4 additional dippings. After the desired thickness is produced, the rubber polymer (KRATON G) latex bag is placed in an oven and cured for 12 hours. If the interior surface was being dipped, then the bag is manipulated to turn the exterior surface right side out. If both surfaces are desired to be treated, the above process is repeated on the untreated surface. After the anti-permeation treatment has been completed, the latex bag is properly outfitted with the straps and the plastic fittings for marketing.

Figure 7:
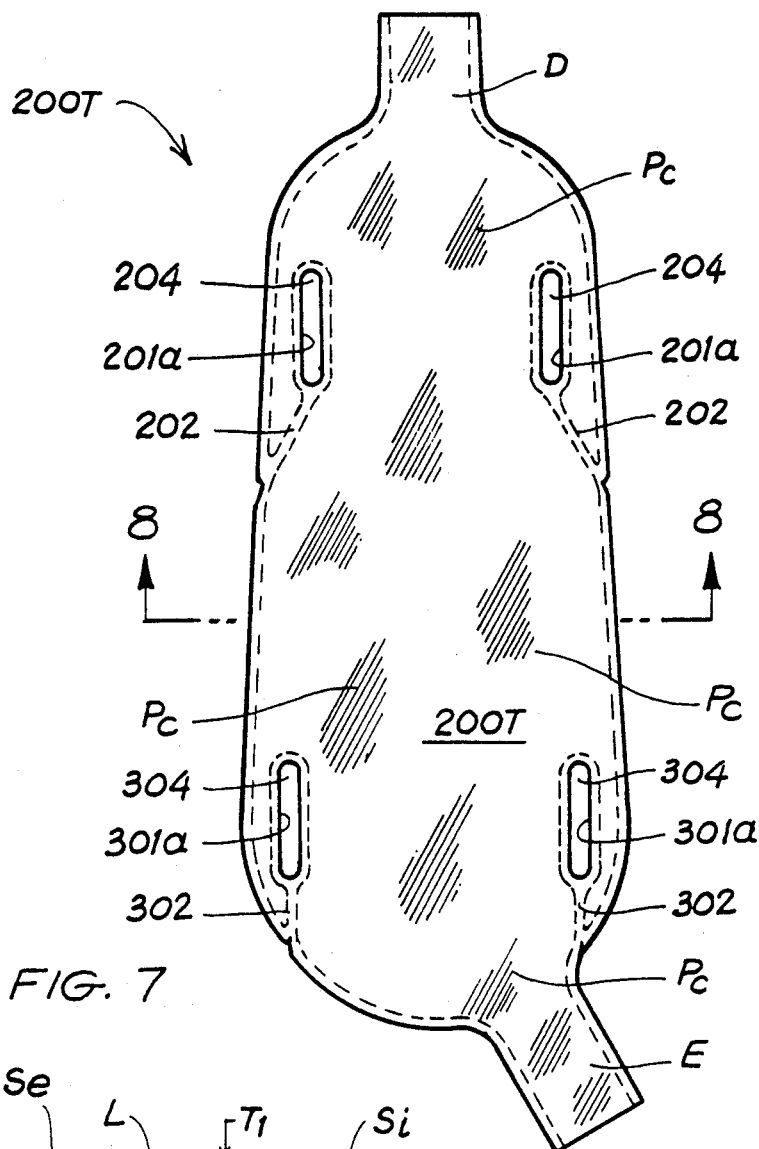
FIG. 7 is a plan view of a flat structured leg bag according to the present invention shown in a formed state without the former (mold) used to produce it, and having a highly impermeable chemical compound treatment in the form of a coating throughout the exterior surface of the bag.
Figure 8:
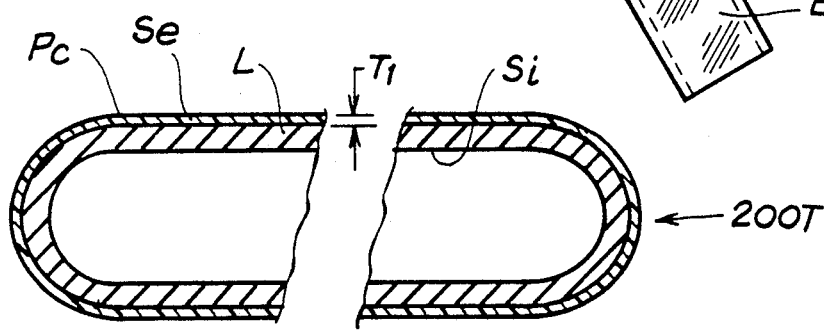
FIG. 8 is a cross-sectional view of the leg bag taken along line 8—8 in FIG. 7 illustrating the latex body structure and the coating of the highly impermeable chemical compound on the exterior surface of the bag.
Figures 8A, 8B:
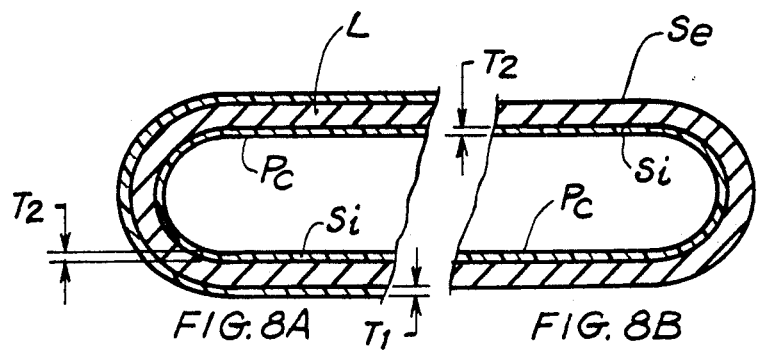
FIG. 8a is a variation of the cross-sectional view shown in FIG. 8 illustrating a partial cross-sectional of a latex bag structure provided with coatings of the highly impermeable chemical compound on both the exterior and interior surfaces of the bag.
FIG. 8b is another variation of the cross-sectional view shown in FIG. 8 illustrating a partial cross-section of a latex bag structure provided with coatings of the highly impermeable chemical compound on interior surface of the bag.

Referring to FIG. 7, an anti-permeation treated latex bag 200T is illustrated having a thermoplastic coating (film) Pc deposited throughout the body of the bag extending from entry port E to a draining port D. The areas more vulnerable to wear are the strap holder inner portion 201a, 301a within the strap holder openings 204, 304. The wear points can be periodically re-treated with a small amount of the KRATON G/toluene cement using a suitable applicator, as noted above. The nodal growth areas 202, 302 have been observed to have a thicker coating of the thermoplastic film, presumably due to the swelling of the latex caused by the solvent action and the subsequent penetration of the KRATON G into the latex surface, also as noted above. FIG. 8 is a cross-section taken along line 8—8 in FIG. 7 and illustrates the thermoplastic coating Pc deposited on an exterior surface Se of the latex bag material L and having a uniform thickness T1. The interior surface Si has not been treated. FIG. 8a shows a section of a latex bag treated with the anti-permeation rubber polymer on both interior and exterior surface. FIG. 8b shows a cross-section of a bag treated only on the interior surface Si and having a film thickness of T2.

Therefore, while the present invention has been shown and described herein in what is believed to be the most practical and preferred embodiments, it is recognized that departures can be made therefrom within the scope of the invention, which scope is therefore not to be limited to the details disclosed herein but is to be accorded the full scope of the claims so as to embrace any and all equivalent apparatus.

I claim:

1. A container apparatus formed from latex, said apparatus comprising:
    a main elongated container portion having at least one strap holder means for attaching securement strapping, said at least one strap holder means comprising strap holder structure that delineates a slot for receiving said securement strapping, said slot having a slot periphery comprised of a periphery portion of said main elongated container portion, a strap holder formation protruding from said main elongated container portion, and a solid nodal growth portion joining said strap holder formation to said periphery portion to form said slot, said solid nodal growth portion being homogeneously cured latex material that extends outwardly from a distal end of said strap holder formation towards said periphery portion of said main elongated container portion.

2. A container apparatus according to claim 1, further comprising:
    a cured rubber polymer coating formed on a surface of said container apparatus, said cured rubber polymer coating comprising a thermoplastic film adhering to said surface, said thermoplastic film being a rubber polymer member remaining after curing a rubber polymer/hydrocarbon solvent solution previously deposited on said surface, said cured rubber polymer coating being formed on said surface to minimize permeation of gases and liquids from within said container apparatus.

3. A container apparatus according to claim 2, wherein:
    said rubber polymer/hydrocarbon solvent solution comprises a solution having a concentration consisting of at least 8 weight percent of a rubber polymer having a styrene-ethylene/butylene-styrene molecular block structure solvated in toluene solvent; and
    said surface comprises an exterior surface of said container apparatus.

4. A container apparatus according to claim 2, wherein:
    said rubber polymer/hydrocarbon solvent solution comprises a solution having a concentration consisting of at least 8 weight percent of a rubber polymer having a styrene-ethylene/butylene-styrene molecular block structure solvated in toluene solvent; and
    said surface comprises an interior surface of said container apparatus.

5. A container apparatus according to claim 2, wherein:
    said rubber polymer/hydrocarbon solvent solution comprises a solution having a concentration consisting of at least 8 weight percent of a rubber polymer having a styrene-ethylene/butylene-styrene molecular block structure solvated in toluene solvent; and
    said surface comprises both an interior surface and exterior surface of said container apparatus.

6. A container apparatus according to claim 2, further comprising:
    at least one skewed port having homogeneous wall structure extending to an interior of said elongated container portion, said at least one skewed port being used for receiving urine via tubing coupled to an incontinent user of said container apparatus, said cured rubber polymer coating being formed to minimize permeation of said urine and associated urine odors from within said container apparatus.

7. A container apparatus according to claim 2, wherein:
    said main elongated container portion being preformed to have a concave body structure that conforms to a shape of a user's leg.

8. A container apparatus according to claim 2, wherein:
    said at least one strap holder means comprise a first and second set of laterally spaced and opposing strap holder means.

9. A container apparatus according to claim 8, wherein:
    said solid nodal growth portion included in said slot periphery of said slot in each of said first set of laterally spaced and opposing strap holder means being oriented substantially parallel with a longitudinal axis of said elongated container portion; and said solid nodal growth portion included in said slot periphery of said slot in each of said second set of laterally spaced and opposing strap holder means being skewed from said longitudinal axis.

10. A container apparatus formed from latex and having a surface treatment to minimize permeation, said apparatus comprising:

a main elongated container portion having at least one strap holder means for attaching securement strapping, said at least one strap holder means comprising strap holder structure that delineates a slot for receiving said securement strapping, said slot having a slot periphery comprised of a periphery portion of said main elongated container portion, a strap holder formation protruding from said main elongated container portion, and a solid nodal growth portion joining said strap holder formation to said periphery portion to form said slot, said solid nodal growth portion being homogeneously cured latex material that extends outwardly from a distal end of said strap holder formation towards said periphery portion of said main elongated container portion; and a cured rubber polymer coating formed on a surface of said container apparatus, said cured rubber polymer coating comprising a thermoplastic film adhering to said surface, said thermoplastic film being a rubber polymer member remaining after curing a rubber polymer/hydrocarbon solvent solution previously deposited on said surface, said cured rubber polymer coating being formed on said surface to minimize permeation of gases and liquids from within said container apparatus.

11. A container apparatus according to claim 10, wherein:

said rubber polymer/hydrocarbon solvent solution comprises a solution having a concentration consisting of at least 8 weight percent of a rubber polymer having a styrene-ethylene/butylene-styrene molecular block structure solvated in toluene solvent; and said surface comprises an exterior surface of said container apparatus.

12. A container apparatus according to claim 11, wherein:

said thermoplastic film having an elasticity that allows at least 700% elongation.

13. A container apparatus formed from latex, said container having a surface treatment to minimize permeation, said apparatus comprising:

a main elongated container portion having at least one strap holder means for attaching securement strapping, said at least one strap holder means comprising strap holder structure that delineates a slot for receiving said securement strapping, said slot having a slot periphery comprised of a periphery portion of said main elongated container portion, a strap holder formation protruding from said main elongated container portion, and a solid nodal growth portion joining said strap holder formation to said periphery portion to form said slot, said solid nodal growth portion being homogeneously cured latex material that extends outwardly from a distal end of said strap holder formation towards said periphery portion of said main elongated container portion; and a cured rubber polymer coating formed on an exterior surface of said container apparatus, said cured rubber polymer coating comprising a thermoplastic film adhering to said surface, said thermoplastic film being a rubber polymer member remaining after curing a rubber polymer/hydrocarbon solvent solution previously deposited on said surface, said cured rubber polymer coating being formed on said surface to minimize permeation of gases and liquids from within said container apparatus, said rubber polymer/hydrocarbon solvent solution comprises a solution having a concentration consisting of at least 8 weight percent of a rubber polymer having a styrene-ethylene/butylene-styrene molecular block structure solvated in toluene solvent.

14. A urine container apparatus formed from latex, said urine container having a surface treatment to minimize permeation of urine odors from within said container, said apparatus comprising:

a cured latex container structure, said cured latex container structure having a cured rubber polymer coating formed on a surface of said container apparatus, said cured rubber polymer coating comprising a thermoplastic film adhering to said surface, said thermoplastic film being a rubber polymer member remaining after curing a rubber polymer/hydrocarbon solvent solution previously deposited on said surface, said cured rubber polymer coating being formed on said surface to minimize permeation of gases and liquids from within said container apparatus.

15. A urine container apparatus according to claim 14, wherein:

said rubber polymer/hydrocarbon solvent solution comprises a solution having a concentration consisting of at least 8 weight percent of a rubber polymer having a styrene-ethylene/butylene-styrene molecular block structure solvated in toluene solvent; and said surface comprises an exterior surface of said container apparatus.

* * * * *